July 4, 1961 O. O. DUNHAM Plant Pat. 2,070
CHRYSANTHEMUM PLANT
Filed Sept. 16, 1959
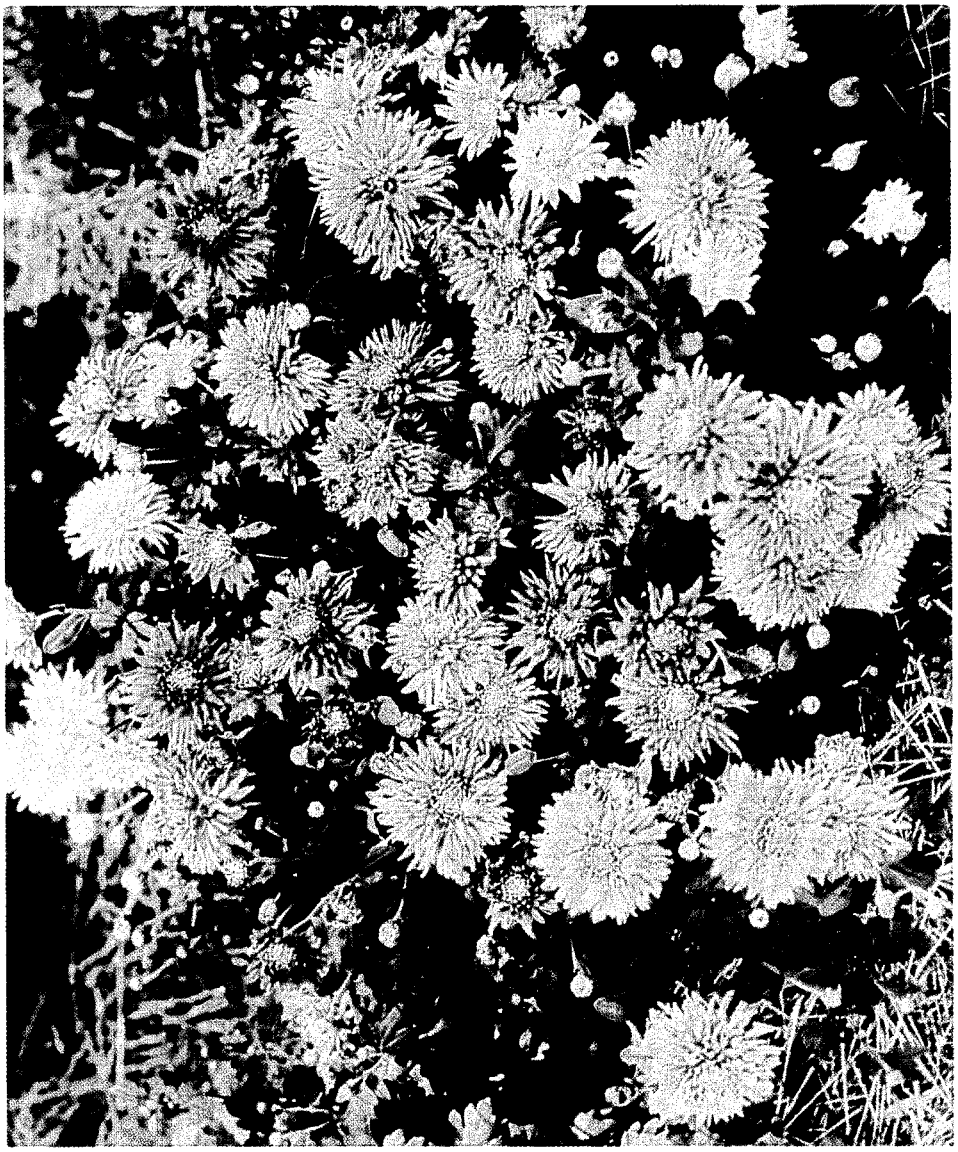
Inventor
O. O. Dunham
by Robb & Robb
attorneys United States Patent Office Plant Pat. 2,070
Patented July 4, 1961

2,070
CHRYSANTHEMUM PLANT

Orville O. Dunham, Rte. 4, Niles, Mich.
Filed Sept. 16, 1959, Ser. No. 840,482
1 Claim. (Cl. 47—60)

My present invention comprises a new and distinct variety of chrysanthemum plant, and is the result of crossing the variety "Apache" (unpatented) with the unpatented variety which I have designated as "No. 5350."

The object of my invention has been to produce a new variety of chrysanthemum plant of the indicum type which will have early and continuous blooming quality of the parent No. 5350 and whose flower form and color derive from the parent "Apache," the blooms in any case as to color and substance being of better quality than both parents or other known varieties.

The present new variety, has resulted from a program of intensive development which I have been conducting for a long period of time involving the careful selection and cross-breeding of various chrysanthemum plants, particularly of the well known so-called American garden chrysanthemum type, crossing the same with plants of the type known as English early chrysanthemums. During this program I have endeavored to take advantage of the continuous early flowering characteristic of the English early chrysanthemums, with the early flowering more compact profuse flowering of the American garden chrysanthemums.

As a result of the specific hybridization previously referred to, I have produced my present new and distinct variety of chrysanthemum plant, characterized by the strong reddish orange blooms of a number of different hues, the very double arrangement of its petals, the large size of its blooms, its better habit and substances and the early, continuous and long blooming period.

More specifically, the blooms of my new variety appear in several different strong reddish orange hues (Nickerson Color Fan published by Munsell Color Company). As grown in the vicinity of Niles, Michigan, under uniform culture, the plants of my new variety grow to an average height of 14 to 18".

My new variety has quite a number of characteristics of both of the parents, but improved characteristics over either separately, and my new variety differs from both of its parents and other known varieties in many respects.

In comparing the color of the blooms of my new variety with the color of the blooms of the variety "Apache," it is noted that the color of the latter appears in the blooms of my new variety, but the several different hues of the blooms on the same plant are not found in "Apache." The petal arrangement in my new variety is somewhat similar to the parent "Apache" but the blooms are more symmetrical than either parent. The petal arrangement of my new variety is very double with many petals and stamens hidden and innumerable petals are found under normal conditions.

Under the conditions of culture previously mentioned, as they have been carried out in the region of Niles, Michigan, plants of my new variety have shown very vigorous growth, somewhat more compact form and upright branching than either of the parents.

My new variety when grown in the region of Niles, Michigan, blooms from early September, somewhat earlier than the seed parent No. 5350, blooming beginning early in September and extending until a killing frost, the blooms appearing in profusion over a long period as previously stated.

The new variety is characterized by its late blooming nature, which is only terminated by a killing frost.

My new variety has been found to retain its distinctive characteristics through successive asexual reproduction which has been effected in the vicinity of Niles, Michigan, by cuttings.

The accompanying drawing forming a part hereof shows a typical plant of my new variety of chrysanthemum plant.

The following is a detailed description of my new variety of chrysanthemum plant, the color references being to the Nickerson Color Fan published by Munsell Color Company;

Parentage: Seedling.
*Seed parent.*—No. 5350 (unpatented).
*Pollen parent.*—"Apache" (unpatented).
Classification: Botanic—*Chrysanthemum indicum.*

*Flower*

Blooming habit: Blooms continuously and profusely from early September until a killing frost, the observations of the plant having been made near Niles, Michigan, during September.

Bud:
*Size.*—Large.
*Form.*—Short with flat top. Not affected by hot or wet weather. Sepals of no consequence.
*Color.*—When petals begin to unfurl—7.5R 4/11. When half blown: inside of petals—7.5R 4/11 washed with 7.5R 5/13; reverse of petals—2.5YR 8/6.
*Calyx.*—Shape—funnel. Size—large. Aspect—hairy.
*Peduncle.*—Length—long. Aspect—rough. Strength—stiff, erect.
*Opening.*—Bud opens well, somewhat affected by adverse conditions.

Bloom:
*Size.*—Large. Average size when fully expanded—4–4½".
*Borne.*—Several together; pyramidal shape.
*Stems.*—Long; strong.
*Form.*—When first open—flat. Permanence—retains its form to the end.
*Petalage.*—Very double. Number of petals under normal conditions innumerable.
*Color.*—Center of flower—7.5R 4/11 washed with 7.5R 5/13. Outer petals—7.5R 5/13 washed with 5R 5/13. Base of petals (singlet)—7.5R 4/11. Inside of petals—7.5R 4/11. Reverse of petals—7.5YR 9/4. General tonality from a distance between 10R 5/11 and 7.5R 5/13. Discoloration: general tonality at end of first week—retains much the same color; second week—2.5YR 6/12; third week—2.5Y 9/9.

Petals:
*Texture.*—Thin; somewhat bleached by hot weather. Fungus infection may occur in wet weather.
*Appearance.*—Inside—velvety. Outside—satiny.
*Form.*—Pointed.
*Arrangement.*—Imbricated.
*Persistence.*—Hang on and dry.
*Lastingness.*—On the plant—very long. As cut flower—very long.

Genital organs:
*Stamens, anthers.*—Small, few. Arrangement—regular around styles.
*Stamens, filaments.*—Medium.
*Styles.*—Columnar, short.
*Stigmas.*—Color—white.
*Ovaries.*—All enclosed in calyx.

*Plant*

Form: Bush.
Growth: Very vigorous, upright, branching, compact.

Foliage:

*Size.*—Large.
*Quantity.*—Normal.
*Shape.*—3 lobed.
*Texture.*—Upper side—glossy, smooth. Under side—velvety. Ribs and veins—ordinary.
*Edge.*—Smooth.
*Leaf stem.*—Under side—velvety.
*Stipules.*—Short.

I claim:

A new and distinct variety of chrysanthemum plant substantially as described herein characterized as to novelty by the strong reddish orange blooms of different hues, the very double arrangement of its petals, the large size of its blooms and the early, continuous and long blooming period.

No references cited.